United States Patent
Geiger et al.

[11] Patent Number: 6,150,941
[45] Date of Patent: Nov. 21, 2000

[54] STAND-OFF NON-INVASIVE ACOUSTIC BABY MONITOR

[75] Inventors: Paul Daniel Geiger, Pomona; Lonnie H. Hudgins, Aliso Viejo, both of Calif.

[73] Assignee: Integrated Medical System, Inc.

[21] Appl. No.: 09/305,900

[22] Filed: May 5, 1999

[51] Int. Cl.[7] ................................................. G08B 23/00
[52] U.S. Cl. ................................ 340/573.1; 340/573.7; 600/453; 600/459
[58] Field of Search ........................... 340/573.1, 573.4, 340/573.7, 575, 527; 600/323, 438, 453, 534, 538, 459; 367/89, 95, 97

[56] References Cited

U.S. PATENT DOCUMENTS

| | | | |
|---|---|---|---|
| 4,122,427 | 10/1978 | Karsh | 600/453 |
| 4,146,885 | 3/1979 | Lawson, Jr. | 340/573.1 |
| 4,836,212 | 6/1989 | Schmitt et al. | 600/480 |
| 4,862,144 | 8/1989 | Tao | 340/573.1 |
| 4,895,160 | 1/1990 | Reents | 600/484 |
| 5,002,060 | 3/1991 | Nedivi | 600/484 |
| 5,105,354 | 4/1992 | Nishimura | 600/484 |
| 5,115,808 | 5/1992 | Popovic et al. | 600/438 |
| 5,370,121 | 12/1994 | Reichenberger et al. | 600/438 |
| 5,385,069 | 1/1995 | Johnson, Jr. | 73/571 |
| 5,388,583 | 2/1995 | Ragauskas et al. | 600/451 |
| 5,479,932 | 1/1996 | Higgins et al. | 600/529 |
| 5,505,199 | 4/1996 | Kim | 600/323 |
| 5,509,414 | 4/1996 | Hok | 600/438 |
| 5,515,865 | 5/1996 | Scanlon | 600/534 |
| 5,590,650 | 1/1997 | Genova | 600/301 |
| 5,853,005 | 12/1998 | Scanlon | 600/459 |
| 5,923,252 | 7/1999 | Sizer et al. | 340/573.1 |

*Primary Examiner*—Daniel J. Wu
*Assistant Examiner*—Van T. Trieu
*Attorney, Agent, or Firm*—Stetina Brunda Garred & Brucker

[57] ABSTRACT

A stand-off, non-invasive acoustic detector for monitoring physical activity and/or breathing activity of children and infants. According to a preferred embodiment, the present invention comprises a two-phase output oscillator coupled to an ultrasonic transmitter and microphone. A respective one of the outputs of the oscillator drives the ultrasonic transmitter, through a power amplifier, which sends out an ultrasound wave. The echo return is picked up by the microphone and thereafter band passed to isolate those frequencies falling within 33 to 40 kHz. Such signal is further adjusted for automatic gain control. The resultant echo return signal is compared to the respective other output of the oscillator, the latter also being adjusted for automatic gain control, which are then combined via a summing junction to produce a resultant signal, the latter being utilized to drive a phase comparator and an alarm timer. To the extent the resultant signal, which corresponds to continuous breathing activity or physical activity, deviates substantially from the signal produced by the comparator for a sufficient length of time, an alarm is activated to signal either abnormal breathing activity or a lack of breathing activity, the latter indicative of either a medical condition, such as SIDS, or the absence of the child from the monitored area.

13 Claims, 1 Drawing Sheet

STAND-OFF NON-INVASIVE ACOUSTIC BABY MONITOR

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

Devices and systems for monitoring the presence and general well-being of children and infants when out of plain view are known in the art. Such devices, typically known as "baby monitors", typically comprise either video cameras and/or audio microphones that are placed in close proximity with the child which transmits a signal to a remote video monitor and/or amplifier/speaker to thus enable the supervising adult to remotely monitor the child/infant. In this regard such systems are designed to provide the supervising adult with a visual and/or auditory signal to the extent the child is uncomfortable or in distress. With respect to most prior art auditory systems, such systems are designed to merely reproduce those sounds emanating from the child/infant, such as crying, coughing and/or choking, which serve as the basis to warn the supervising adult that attention is needed.

Although generally effective in monitoring the condition of a child/infant from a remote location, most prior art systems currently in use suffer from numerous drawbacks. With respect to video monitoring systems, it is known that the cameras utilized to generate the image of the monitored child are typically mounted in fixed position and can only monitor a limited area, such as a crib, for example. As such, to the extent the child strays from such limited field of vision or is covered in bedding, such as blankets, no monitoring capabilities are possible. Likewise, it is known that such video systems are expensive and rather complex, which consequently has limited their widespread use in the home.

Similarly, acoustic monitoring systems suffer from the drawbacks of not providing consistent, uniform and dependable monitoring of a child. In this regard, such systems are based upon the child producing an audible signal, such as a scream or a cough, when such child is in distress or discomfort. However, such systems fail to address a number of situations where a supervising adult must necessarily be warned about conditions beyond those sounds generated in the child's environment. For example, such audio monitors fail to provide any indication should the child quietly leave his or her bed or simply stop breathing, which occurs with Sudden Infant Death Syndrome (SIDS) where a healthy infant dies suddenly during sleep, for no apparent reason.

In addition to failing to provide an adequate degree of monitoring activity, prior art child/infant monitoring systems further have the drawback of repeatedly generating false alarm signals. The most prevalent of such prior art systems are commonly referred to as apnea monitors, which monitor the breathing of an infant in order to detect if apnea occurs (i.e., the cessation of voluntary breathing). In this regard, to the extent the child deviates from rigorous respiratory and metabolic parameters, the apnea monitor generates an alarm signal to alert the supervising adult of the presumably fatal condition. Due to the rigorous parameters within such apnea monitors operate, and given the tendency of such devices to generate alarm signals in the interest of caution, there is thus generated repeated false alarm signals which, in view of the high level of anxiety experienced by parents of children, and particular parents of children who have been determined to be at high risk for SIDS, has caused much anguish in the parents so as to reduce their true efficacy.

In an attempt to reduce the occurrence of false alarms and provide a more dependable monitoring system, several alternative products have been developed for use in the home. The most prevalent of these products include active monitoring devices where a sensor is physically in contact with the child/infant that directly monitors one or more physiological functions, such as breathing, heart rate, etc. Such systems, however, have fallen out of favor due to the requirement to directly attach the sensor(s) to the child/infant insofar as the same have been shown to be uncomfortable and potentially dangerous to the child.

Accordingly, there is a strong need in the art for a child/infant monitoring device which can detect the physiological presence of a living baby that does not require any contact with the child, yet can reliably function under all conditions that would normally be associated with the baby's environment (i.e., room). Furthermore, there is a need in the art for a child/infant monitoring device that can be utilized either alone or in combination with existing monitoring devices that is particularly effective in monitoring passive breathing activity, which can occur when the child/infant is still or asleep, and can further monitor such activity when the child/infant is covered in one or more layers of material, such as bedding, blankets, and the like. There is likewise a need in the art for a child/infant monitoring system that can be utilized to monitor the presence and well-being of a child/infant that utilizes existing technology, provides superior monitoring capability with reduced occurrences of false alarms, is inexpensive to manufacture, easy to deploy and may be readily fabricated from existing, commercially available components.

BRIEF SUMMARY OF THE INVENTION

The present invention specifically addresses and alleviates the above-identified deficiencies in the art. In this regard, the present invention is directed to a stand-off, non-invasive acoustic detector for monitoring the continuous breathing or other movement of a child/infant and to provide an alarm to the extent such activity is no longer detected or changes dramatically. According to a preferred embodiment, the monitoring system comprises an oscillator capable of producing two-phase outputs in the frequency range of approximately 33–40 kHz for both sine $\omega_o t$ and cosine $\omega_o t$. The oscillator is operatively coupled to the ultrasonic transmitter such that a respective one of either the sine or cosine signals generated by the oscillator drives the ultrasonic transmitter, via an amplifier, such that the ultrasonic transmitter sends out an ultrasound wave over a given area, such as a crib. A microphone picks up the echo return of the ultrasound wave, which is subsequently band-passed such that only those sounds are identified the frequency content of which lies between approximately 33 to 40 kHz. Thereafter, the output is adjusted for automatic gain control and processed to generate an echo return signal. The respective other signal generated by the oscillator is subsequently mixed with the echo return signal, via a summing junction, to produce a resultant signal which corresponds to any physical motion, and in particular breathing, within the microphone's field of sensitivity.

The resultant signal is then adjusted for automatic gain control and squared with an analog computer, with the resultant output then driving a phase comparator, the latter comparing the signal generated by the echo return indicative of continuous activity with a reference indicative of a lack of activity, and an alarm timer. To the extent the resultant signal fails to indicate continuous motion, and in particular breathing, within a predetermined period of time, the alarm portion is eventually activated to provide a warning that the baby's motion is no longer detected. Advantageously, due to the fact that the system of the present invention is utilized to identify and monitor a narrow band of ultrasound frequencies indicative of child/infant motion or breathing activity, the system of the present invention is able to narrowly focus on such sounds without distortion or interference from unrelated sounds or background noise of differing frequencies, which typically occurs in a household setting. The present invention has the further advantage of being able to detect normal breathing sounds/patterns irrespective of the child's orientation within a crib or bed-type setting, as well as whether or not the child is covered by one or more blankets.

It is therefore an object of the present invention to provide a stand-off, non-invasive, acoustic detector device that is capable of monitoring infant/child motion and normal breathing patterns and produce an alarm to the extent a given child's/infant's motion is no longer detected.

Another object of the present invention is to provide a stand-off, non-invasive, acoustic monitor that, in addition to monitoring breathing activity, can accurately provide an indication as to whether a child/infant is present within a given vicinity.

Another object of the present invention is to provide a stand-off, non-invasive, acoustic monitor that provides consistent, uniform and dependable monitoring of a child/infant that substantially reduces, if not eliminates, false alarm signals generated thereby.

Another object of the present invention is to provide a stand-off, non-invasive, acoustic monitor that can be either utilized separately or in combination with existing conventional monitoring equipment to provide a comprehensive visual and/or acoustic monitoring system.

Still further objects of the present invention include providing a stand-off, non-invasive, acoustic monitor that is inexpensive and of relatively simple construction, may be readily fabricated from existing components, may be easily and readily deployed and has greater sensitivity and detection capabilities than prior art systems, particularly in monitoring passive activity, such as sleep.

BRIEF DESCRIPTION OF THE DRAWING

These, as well as other features of the present invention will become more apparent upon reference to the drawing wherein.

DETAILED DESCRIPTION OF THE INVENTION

Figure 1:
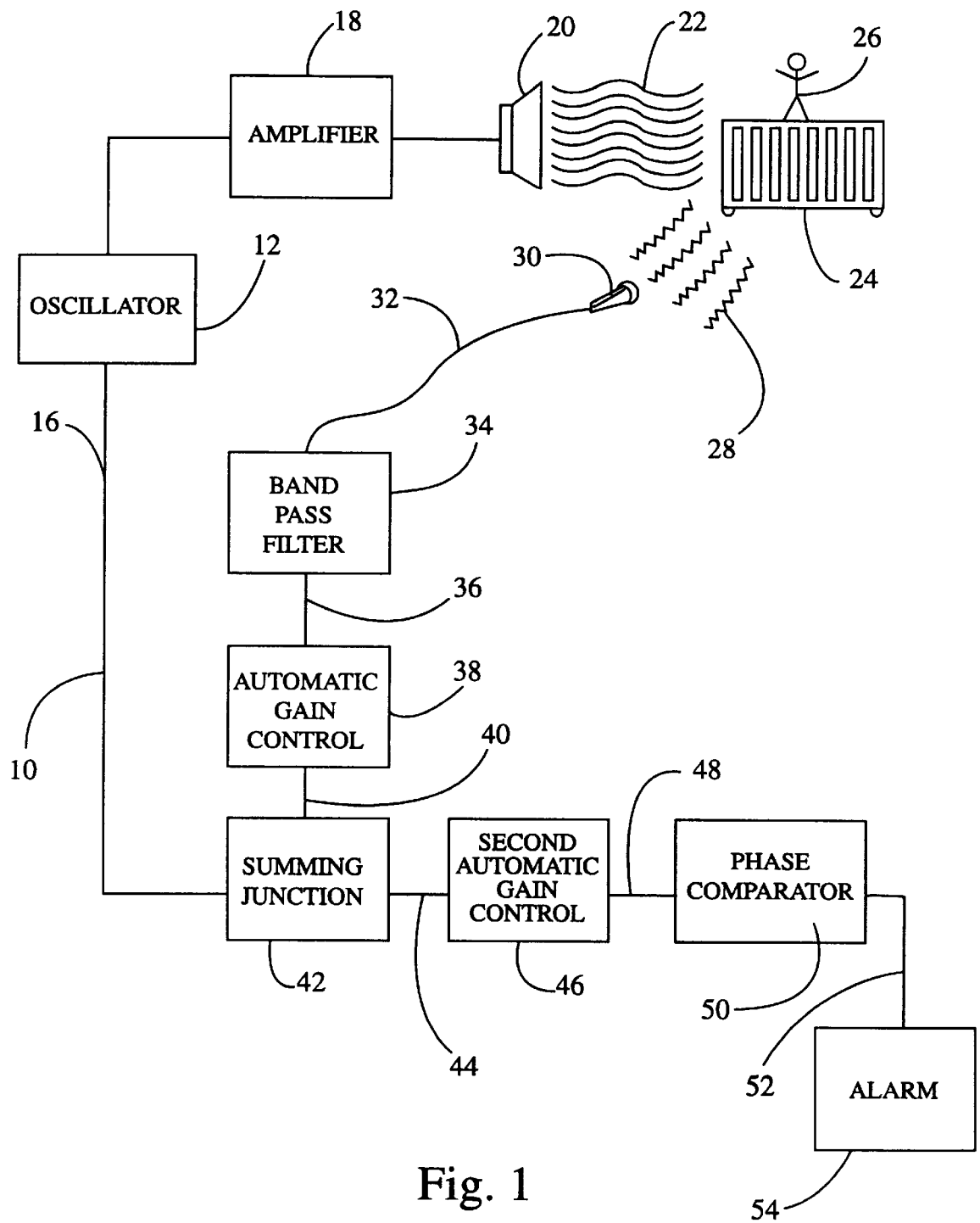
FIG. 1 is a block diagram showing the components of a stand-off acoustic monitor as constructed according to a preferred embodiment of the present invention.

The detailed description as set forth below in connection with the appended drawings is intended as a description of the presently preferred embodiments of the invention, and is not intended to represent the only form in which the present invention may be constructed or utilized. The description sets forth the functions and sequences of steps for constructing and operating the invention in connection with the illustrated embodiments. It is understood, however, that the same or equivalent functions and sequences may be accomplished by different embodiments and that they are also intended to be encompassed within the scope of this invention.

Referring now to FIG. 1, there is shown a block diagram identifying the general components of the monitoring system 10 of the present invention. The system 10 is specifically designed to continuously monitor physiological activity utilizing continuous-wave Doppler ultrasound. The system 10 is particularly suited to continuously monitor breathing activity of children/infants and to generate an alarm signal to the extent such monitored activity significantly deviates from normal activity or, alternatively, ceases altogether. With respect to the later scenario, it is believed that the system 10 of the present invention is particularly well-suited for monitoring children/infants who are at risk for SIDS, and even for determining the physical presence of the child in the area monitored thereby.

As illustrated, the system 10 comprises an oscillator 12 which provides continuous two-phase outputs 14, 16 for both $\sin \omega_o t$ or $\cos \omega_o t$, with a fixed center frequency between approximately 33–40 kHz. As is known, such oscillator may take the form of any well-known in the art. A respective one 14 of the signals 14, 16 is fed to a power amplifier 18, the latter driving an ultrasonic transmitter 20, the latter preferably comprising a wide-angle continuous-wave ultrasonic transmitter, to produce an ultrasonic output 22 having a frequency between approximately 33 and 40 kHz. The ultrasonic transmitter 20 is preferably oriented to continuously broadcast the ultrasonic output 22 over an area at least as wide as two feet by three feet or other similar dimensions that closely approximate the size of most cribs or child bedding 24. In this regard, the ultrasonic transmitter 20 should be at least capable of producing an output 22 that substantially covers the area within which a child 26 will be confined.

As will be recognized by those skilled in the art, once the output 22 is broadcast upon the crib 24 or other area containing the child 26 sought to be monitored, an echo return 28 will be produced, the latter being picked up by a microphone receiver 30. Such microphone receiver may take any of a variety of those known in the art, including those produced by Brüel & Kjær of Denmark. As will be recognized, however, any microphone 30 utilized in the practice of the present invention must be capable of detecting frequencies within the range of 33 to 40 kHz and, according to the most preferred embodiment, frequencies of about 40 kHz.

In this regard, it has recently been identified that the echo return of frequencies falling within the range of 33 to 40 kHz can detect small chest motion caused by a child's breathing with great accuracy. It has further been advantageously found that such range of frequencies can detect such small chest motion irrespective of the orientation of the child, as well as whether or not the child is covered by one or more layers of blankets formed from normal blanket material. Indeed, the echo return of frequencies falling within such range of frequencies, and in particular 40 kHz, is indicative of motion caused by physiological activity such as breathing, and therefore reliably detects the presence of a living child. Of further advantage is the fact that such frequencies, because they fall within the ultrasonic spectrum, are beyond human hearing capability, and thus cannot be confused with other audible sounds, such as background noise and the like, which may emanate within or around the child's environment, discussed more fully below.

The output 32 of microphone 30 is then passed through a band pass filter 34 which serves to pass only frequencies within the 33 to 40 kHz range, thus removing sounds detected by the microphone 30 that are produced from the surrounding environment, but not indicative of the breathing motion produced by the child/infant 26. Advantageously, unlike prior art monitoring systems that merely reproduce all the sounds within the child's environment, which can include other people talking within the vicinity of the monitor, barking dogs, television noise, and the like, the present invention focuses exclusively on a narrow range of frequencies that are limited exclusively to the specific physiological function of breathing.

The resultant signal 36 is further modified via automatic gain control 38 to produce an output 40 having a uniform amplitude or energy. Such signal 40 is fed to a summing junction 42 which subtracts the carrier signal 16 generated by oscillator 12 to produce a further output 44, the latter representing the variable portion of the echo return signal.

As will be appreciated by those skilled in the art, output 44 is indicative of the monitored child's/infant's constant breathing activity, and should correspond to any physical motion within the field of monitoring capability of the system 10 of the present invention. The resultant signal 44 is then fed to a second automatic gain control 46, and may thereafter be squared with an analog computer (not shown), with the resultant signal 48 being used to drive a phase comparator 50. The phase comparator 50 continuously monitors the variable portion of the echo return signal as reflected in signal 48, which is indicative of physiological activity/breathing, with a reference signal generated internally, which may comprise a simple sine or cosine wave.

To the extent the variable portion of the echo return signal, as provided by signal 48, deviates from the reference signal generated within the phase comparator 50 for a sufficient length of time that can range from a few seconds to preferably no more than one minute, as determined by an internal timer coupled to the phase comparator (not shown), a resultant signal 52 will be generated which sounds an alarm 54. In this respect, it is contemplated that to the extent the echo return signal does not indicate any variable activity, indicative of physical activity, breathing, etc., indicative of normal chest sounds, a situation will arise where either the child has stopped breathing or has wandered away from the area being monitored, which in any event requires the intervention of the supervising adult. It is further contemplated that the system of the present invention may be modified that to the extent the child's monitored breathing activity becomes abnormal or erratic, which can happen during hyper-ventilation or an asthmatic attack, it is believed that the signal 48, when compared to reference signal generated by the phase comparator 50, will also produce an alarm signal 52 to the extent such abnormal activity occurs for a sufficient length of time (e.g., 10 seconds to one minute), as determined by an internal timer (not shown) housed within the comparator 50.

It is believed that the system 10 of the present invention may be utilized either by itself or, alternatively, may be utilized in combination with conventional monitoring equipment, such as video and auditory monitoring systems. In this respect, it is believed that the system 10 of the present invention is particularly well-suited for use in combination with such prior art devices insofar as such prior art devices are generally effective in monitoring sounds and perceptible activity, but are ill-suited to produce any kind of signal in the absence of activity. As is a well-recognized problem in the art, however, such lack of activity, often mistaken for sleeping, can be indicative the more serious problem of SIDS or the absence of the child/infant from the monitored area.

Although the aforementioned layout of components depicted in FIG. 1 is illustrative of one preferred embodiment of the present invention, it will be recognized by those skilled in the art that alternative methodologies for applying continuous-wave Doppler ultrasound to infant monitoring can likewise be successfully applied. In this respect, it will be appreciated by those skilled in the art that applying and monitoring continuous-wave Doppler ultrasound can be achieved through the use of well-known and readily available monitoring equipment, including, but not limited to, phase detectors, discriminators, phase-locked loops, carrier differencer, In-phase and Quadrature phase (I&Q) detectors, synchronous demodulators, mixers, and phase comparators. As will be recognized, in all such methodologies there can be easily and readily derived a practical measurement of small phase changes in a monitored echo return signal, and how such differences, when utilized to monitor the activity of a specific physiological function, can provide superior monitoring capabilities of such physiological function than has been heretofore available.

Although the invention has been described herein with specific reference to a presently preferred embodiment thereof, it will be appreciated by those skilled in the art that various modifications, deletions, and alterations may be made to such preferred embodiment without departing from the spirit and scope of the invention. For example, it will be recognized that the frequency range monitored, 30–40 kHz, could be shifted to a higher or lower range to achieve a similar result. Accordingly, it is intended that all reasonably foreseeable additions, modifications, deletions and alterations be included within the scope of the invention as defined in the following claims.

What is claimed is:

1. An infant monitoring system for continuously monitoring the breathing of an infant and producing an alarm whenever the breathing activity of the infant is in jeopardy comprising:

a) an apparatus for generating an ultrasound wave and broadcasting said ultrasound wave upon said infant such that an echo return of said ultrasound wave is generated from said infant;

b) a microphone for detecting the echo return of said ultrasound wave and generating a first signal corresponding thereto;

c) an apparatus for generating a second signal, said second signal representing normal respiratory activity anticipated for an infant;

d) a phase comparator for comparing said first signal with said second signal and measuring the degree of variation between said first signal and said second signal, said phase comparator further being designed to transmit a third signal at intervals corresponding to when said first signal deviates from said second signal beyond a respective one of a plurality of selected degrees of variation between said first signal and said second signal, wherein each respective one of said selected degrees of variation corresponds to an abnormal respiratory condition;

e) a timer for timing the duration of the receipt of the third signal generated from said phase comparator; and f) an alarm coupled to said timer, said alarm being designed to produce an alarm signal whenever said timer indicates receipt of said third signal from said phase comparator for a reference time duration.

2. The system of claim 1 wherein said apparatus for generating and broadcasting said ultrasound wave produces and broadcasts an ultrasound wave having a frequency falling between 33 and 40 kHz.

3. The device of claim 2 wherein said ultrasound wave is generated by the operative combination of an oscillator capable of producing a phase output signal, an amplifier, and an ultrasonic transmitter.

4. The system of claim 3 wherein said ultrasonic transmitter comprises a wide-angle continuous-wave ultrasonic transmitter.

5. The system of claim 3 wherein said oscillator further generates a carrier signal.

6. The system of claim 5 wherein said signal for producing said ultrasound wave and said carrier signal produced by said oscillator comprise dedicated ones of continuous two-phase outputs generated by said oscillator.

7. An infant monitoring system for continuously monitoring the breathing of an infant and producing an alarm whenever the breathing activity of the infant is in jeopardy comprising:
   a) an apparatus for generating an ultrasound wave and broadcasting said ultrasound wave upon said infant such that an echo return of said ultrasound wave is generated from said infant;
   b) a microphone for detecting the echo return of said ultrasound wave and generating a first signal corresponding thereto;
   c) an apparatus for generating a second signal;
   d) a summing junction for combining said first and second signals to produce a resultant third signal;
   e) a phase comparator operatively coupled to said summing junction for receiving said third signal and comparing said third signal with an internally generated reference signal wherein said reference signal represents normal respiratory activity anticipated for an infant, said phase comparator further being designed to measure the degree of variation between said third signal and said reference signal and transmit a fourth signal whenever said third signal deviates from said reference signal beyond at least one of a plurality of selected degrees of variation between said first signal and said second signal, wherein each respective one of said selected degrees of variation corresponds to an abnormal respiratory condition;
   f) a timer operatively coupled to said phase comparator for timing the duration the fourth signal is generated from said phase comparator; and
   g) an alarm coupled to said timer, said alarm being designed to produce an alarm signal whenever said timer indicates generation of said fourth signal from said phase comparator beyond a reference time duration.

8. The system of claim 7 wherein said apparatus for generating and broadcasting said ultrasound wave produces and broadcasts an ultrasound wave falling between 33 and 40 kHz.

9. The system of claim 8 wherein said system further comprises:
   g) a band pass filter operatively coupled intermediate said microphone and said summing junction, said band pass filter being designed to pass only frequencies picked up from microphone falling within 33 to 40 kHz.

10. The system of claim 1 and the system of claim 8 wherein said timer actuates said signal for generating said alarm when said period of time said timer receives said third signal exceeds 10 seconds.

11. A method for continuously monitoring the breathing of an infant and producing an alarm whenever the breathing activity of the infant is in jeopardy comprising the steps:
   a) generating an ultrasound wave and broadcasting said ultrasound wave upon said infant such that an echo return of said ultrasound wave is generated from said infant;
   b) detecting said echo return of said ultrasound wave and generating a first signal corresponding thereto;
   c) generating a second signal, said second signal representing normal respiratory activity anticipated for an infant;
   d) providing a plurality of reference levels corresponding to dedicated degrees of variation between said first signal and said second signal, wherein each respective one of said dedicated degrees of variation correspond to a specific respiratory abnormality;
   e) selecting at least one reference level provided in step d);
   f) comparing said first signal with said second signal and measuring the degree of variation between said first signal and said second signal;
   g) measuring the degree and duration said first signal deviates from said second signal to said degree selected in step e and producing a third signal;
   h) timing the duration said third signal is generated; and
   i) producing an alarm signal whenever the duration in step h) exceeds a duration of 10 seconds.

12. The method of claim 11 wherein in step a), said ultrasound wave has a frequency falling between 33 and 40 kHz.

13. The method of claim 11 wherein in step b), said first signal is filtered to exclude any frequencies falling below 33 kHz and above 40 kHz.

* * * * *